US010316006B2

(12) United States Patent
Moganty et al.

(10) Patent No.: US 10,316,006 B2
(45) Date of Patent: Jun. 11, 2019

(54) HETEROCYCLIC IONIC LIQUIDS

(71) Applicant: NOHMs Technologies, Inc., Rochester, NY (US)

(72) Inventors: Surya Moganty, Henrietta, NY (US); Luigi Abbate, Rochester, NY (US); Gabriel Torres, Rochester, NY (US); Kevin Brown, Rochester, NY (US); John Sinicropi, Rochester, NY (US)

(73) Assignee: NOHMS Technologies, Inc., Rochester, NY (US)

(*) Notice: Subject to any disclaimer, the term of this patent is extended or adjusted under 35 U.S.C. 154(b) by 38 days.

(21) Appl. No.: 15/494,072

(22) Filed: Apr. 21, 2017

(65) Prior Publication Data
US 2017/0305869 A1 Oct. 26, 2017

Related U.S. Application Data

(60) Provisional application No. 62/326,283, filed on Apr. 22, 2016.

(51) Int. Cl.
H01M 10/0565 (2010.01)
H01M 6/18 (2006.01)
C08F 14/00 (2006.01)
C08F 28/02 (2006.01)
C07D 295/15 (2006.01)
H01M 10/0525 (2010.01)
H01M 10/0567 (2010.01)
H01M 10/0569 (2010.01)
H01M 10/0566 (2010.01)

(52) U.S. Cl.
CPC ...... C07D 295/15 (2013.01); H01M 10/0525 (2013.01); H01M 10/0566 (2013.01); H01M 10/0567 (2013.01); H01M 10/0569 (2013.01); H01M 2300/0025 (2013.01)

(58) Field of Classification Search
CPC ......... H01M 10/0569; H01M 10/0525; H01M 10/0567; C07D 295/15; C09K 3/00
See application file for complete search history.

(56) References Cited

U.S. PATENT DOCUMENTS 8,345,407 B2     1/2013  Seddon et al.
2008/0296531 A1 12/2008  Whiston et al.
2010/0028785 A1* 2/2010  Choi ............... H01M 10/0525
                                                 429/337
2014/0113202 A1* 4/2014  Sun ................ H01M 10/052
                                                 429/328

(Continued)

FOREIGN PATENT DOCUMENTS

EP        2162435 B1     9/2013

OTHER PUBLICATIONS

Salem et al., "Room Temperature Ionic Liquid Electrolytes Based on Azepanium Imide Salts for Lithium Batteries", Journal of the Electrochemical Society, 159 (2), A172-A176, Dec. 22, 2011.*

(Continued)

Primary Examiner — Kenneth J Douyette
(74) Attorney, Agent, or Firm — Bond, Schoeneck & King, PLLC; Joseph Noto

(57) ABSTRACT

An ionic liquid compound includes an azepanium-functionalized cation. An electrochemical cell electrolyte for an electrical energy storage device includes the ionic liquid compound, aprotic organic solvent, alkali metal salt and an additive.

5 Claims, 2 Drawing Sheets

(56) References Cited

U.S. PATENT DOCUMENTS

2015/0207176 A1    7/2015   Moganty et al.
2015/0333374 A1   11/2015   Moganty et al.

OTHER PUBLICATIONS

Belhocine et al. (2011) "New ionic liquids from azepane and 3-methyulpiperidine exhibiting wide electrochemical windows," Green Chem. vol. 13, pp. 59-63.
Belhocine et al. (2011) "Azepanium ionic liquids," Green Chem. vol. 13, pp. 3137-3155.
PCT International Search Report, Form PCT/ISA/210, International application No. PCT/US17/28907, International filing date Apr. 21, 2017, dated Jul. 17, 2017.

\* cited by examiner

HETEROCYCLIC IONIC LIQUIDS

CROSS REFERENCE

This application claims the benefit of the filing date of U.S. Provisional Patent Application Ser. No. 62/326,283, filed Apr. 22, 2016 which is hereby incorporated by reference in its entirety.

FIELD

This disclosure is directed towards ionic liquid compounds whose cations have at least one azepanium functional moiety, and more particularly to the use of the ionic liquid compounds in high performance, nonflammable, wide operating temperature range electrolyte formulations for electrochemical cells.

BACKGROUND

Recent progress in synthesis and electrochemical analysis of room temperature ionic liquids (ILs) has established the promise of this unique class of materials as electrolytes for next-generation Li-ion batteries. ILs are organic salts having melting points below 100° C. and generally consist of a bulky cation and an inorganic anion. The large cation size allows for delocalization and screening of charges, resulting in a reduction in the lattice energy and thereby the melting point or glass transition temperature. ILs have unique physicochemical properties such as negligible vapor pressure, non-flammability, good room-temperature ionic conductivity, wide electrochemical window, and favorable chemical and thermal stability. These properties are desirable for providing IL-based electrolytes for lithium batteries. The vast range of anion and cation chemistries that can be combined to create tailor-made or explicitly designed ILs to complement a specific combination of electrode chemistries also provides a largely untapped materials library that can address concerns regarding battery safety.

Recently, ionic liquids mixed with organic solvents such as ethylene carbonate (EC), diethyl carbonate (DEC) and lithium salts were investigated as thermally stable Li-ion electrolytes (Montanino et al., J Power Sources, 194, 601, 2009). The blending of ionic liquids with conventional electrolytes yielded thermally stable non-flammable electrolytes. However, this work did not address the critical issue of graphite anode protection in the presence of ionic liquids.

The intercalation of Li ions into the graphite basal planes occurs around 0.1 V vs Li/Li+, which is beyond the thermodynamic stability of the organic electrolytes. During this process, the graphite electrode is cathodically polarized to low potential, and electrolyte solvent, salt anions and impurities in the electrolyte are reduced to form insoluble products that are deposited on the surface of the anode to form a passivating layer. This process takes place mostly during the first several cycles of a working battery. Thus, the formed passivating layer, as known as a solid electrolyte interface (SEI) layer (Peled et al., Journal of The Electrochemical Society, 126, 2047, 1979), is crucial for the performance of Li-ion batteries. The nature and behavior of the SEI layer affects the cycle life, rate capability, shelf life and safety of Li-ion batteries. Although ILs are stable at high voltages, their cathodic stability is poor. Thus, one of the challenges is to widen the cathodic stability window of ILs to enable the use of a graphite anode.

The use of pure imidazolium-based ILs as an electrolyte solvent is limited by poor cathodic stability, 1 V vs Li/Li+ (Choi et al., Angewandte Chemie International Edition, 51, 9994, 2012). The more cathodically stable ammonium cation-based ILs suffer from co-intercalation of the IL cations into the graphite structure at higher potentials than the Li ion intercalation potential (M. Ishikawa, ECS Transcations, 50(26), 317, 2013; Y. An et al., RSC Advances, 2, 4097, 2012). Recent studies show that pyrrolidinium and piperidinium cation-based ILs exhibit lower reductive potentials than their more popular imidazolium counterparts. These cations also exhibit similar co-intercalation behavior. Maolin et al. (Journal of Chemical Physics, 128, 134504, 2008), using molecular dynamic (MD) simulations of IL on a graphite surface, reported that the butyl group on the imidazolium cation aligned parallel to the graphite surface.

Salem and Abu-Lebdeh (Journal of The Electrochemical Society 161, A1593, 2014) reported the comparison of ionic liquids with different ring sizes of cyclic ammonium cations (pyrrolidinium, piperidinium and azepanium). The disclosure of Salem and Abu-Lebdeh relates to ring size and electrochemical stability. However, they did not find any correlation between ring size and corresponding electrolyte performance in Li-ion cells. Similarly, Belhocine et al., (Green Chemistry 13, 3137, 2011) disclosed alkyl-substituted and ether functional group-substituted azepanium cation-based ionic liquids, but did not contemplate using the synthesized ionic liquids as electrolytes in combination with co-solvents.

These results indicate the importance of understanding the interfacial characteristics of ionic liquids on solid electrode surfaces. Therefore, there is a need to incorporate a novel ionic liquid to form more stable and well-regulated layers at graphite or other anode surfaces of electrodes.

SUMMARY

In accordance with one aspect of the present disclosure, there is provided an electrolyte in an electrical energy storage device, the electrolyte including an aprotic organic solvent, an alkali metal salt, an additive and an ionic compound that contains the azepanium functional moiety.

In accordance with another aspect of the present disclosure, there is provided an electrolyte in an electrical energy storage device, the electrolyte including an aprotic organic solvent, an alkali metal salt, an additive and an ionic compound that contains the azepanium functional moiety, wherein the aprotic organic solvent is open-chain or cyclic carbonates, carboxylic acid esters, nitrites, ethers, sulfones, sulfoxides, ketones, lactones, dioxolanes, glymes, crown ethers, siloxane, phosphoric acid ester, phosphates, phosphites mono- or polyphosphazene or mixtures thereof.

In accordance with another aspect of the present disclosure, there is provided an electrolyte in an electrical energy storage device, the electrolyte including an aprotic organic solvent, an alkali metal salt, an additive and an ionic compound that contains the azepanium functional moiety, wherein the cation of the alkali metal salt is lithium, sodium, aluminum or magnesium.

In accordance with another aspect of the present disclosure, there is provided an electrolyte in an electrical energy storage device, the electrolyte including an aprotic organic solvent, an alkali metal salt, an additive and an ionic compound that contains the azepanium functional moiety, wherein the additive is a sulfur-containing compound, phosphorous-containing compound, a boron-containing compound, a silicon-containing compound, a nitrogen-containing heterocyclic compound, a compound containing unsaturated carbon-carbon bonds, carboxylic acid anhydrides or mixtures thereof.

In accordance with another aspect of the present disclosure, there is provided an ionic liquid compound including a cation and an anion according to formula:

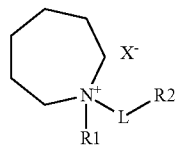

wherein $R_1$ is selected from the group including $C_1$-$C_{16}$ alkyl, alkenyl, alkoxy, aryl, alkynyl, alkylsiloxy, alkylhalide, silyl, ester, carbonyl, phenyl or perfluoro group;

wherein L is a linker including $C_1$-$C_{16}$ alkyl, alkenyl, alkoxy, aryl, alkynyl, alkylsiloxy, alkylhailde, thioether, sulfoxide, azo, amino, silyl, ester, carbonyl, phenyl or perfluoro group;

wherein $R_2$ represents a functional moiety including halide, oxygen, nitrogen, sulfur, phosphorus, partially or fully halogenated alkyl, ketone, carbonyl, alkene, aryl, nitrile, silane, sulfone, thiol, phenol, hydroxyl, amine, imide, aldehyde, carboxylic acid, alkyne, carbonate or anhydride, wherein any of the carbon or hydrogen atoms in the moieties are further substituted with halide, oxygen, nitrogen, sulfur, phosphorus, ester, ketone, carbonyl, alkene, aryl, nitrile, silane, sulfone, thiol, phenol, hydroxyl, amine, imide, aldehyde, carboxylic acid, alkyne, carbonate or anhydride; and wherein $X^-$ represents an anion of the ionic compound including a halide, aluminate, arsenide, cyanide, thiocyanate, nitrite, benzoate, chlorate, chlorite, chromate, sulfate, sulfite, silicate, thiosulfate, oxalate, acetate, formate, hydroxide, nitrate, phosphate, imide, borate or phosphazines.

In accordance with another aspect of the present disclosure, there is provided an electrolyte in an electrical energy storage device, the electrolyte including:
a) an aprotic organic solvent system;
b) an alkali metal salt;
c) an additive; and
d) an ionic liquid compound including a cation and an anion according to formula:

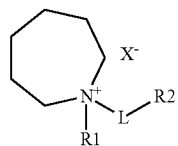

wherein $R_1$ is selected from the group including $C_1$-$C_{16}$ alkyl, alkenyl, alkoxy, aryl, alkynyl, alkylsiloxy, alkylhalide, silyl, ester, carbonyl, phenyl or perfluoro group;

wherein L is a linker including $C_1$-$C_{16}$ alkyl, alkenyl, alkoxy, aryl, alkynyl, alkylsiloxy, alkylhailde, thioether, sulfoxide, azo, amino, silyl, ester, carbonyl, phenyl or perfluoro group;

wherein $R_2$ represents a functional moiety including halide, oxygen, nitrogen, sulfur, phosphorus, partially or fully halogenated alkyl, ketone, carbonyl, alkene, aryl, nitrile, silane, sulfone, thiol, phenol, hydroxyl, amine, imide, aldehyde, carboxylic acid, alkyne, carbonate or anhydride, wherein any of the carbon or hydrogen atoms in the moieties are further substituted with halide, oxygen, nitrogen, sulfur, phosphorus, ester, ketone, carbonyl, alkene, aryl, nitrile, silane, sulfone, thiol, phenol, hydroxyl, amine, imide, aldehyde, carboxylic acid, alkyne, carbonate or anhydride; and wherein $X^-$ represents an anion of the ionic compound including a halide, aluminate, arsenide, cyanide, thiocyanate, nitrite, benzoate, chlorate, chlorite, chromate, sulfate, sulfite, silicate, thiosulfate, oxalate, acetate, formate, hydroxide, nitrate, phosphate, imide, borate or phosphazines.

These and other aspects of the present disclosure will become apparent upon a review of the following detailed description and the claims appended thereto.

DETAILED DESCRIPTION

Figure 1:
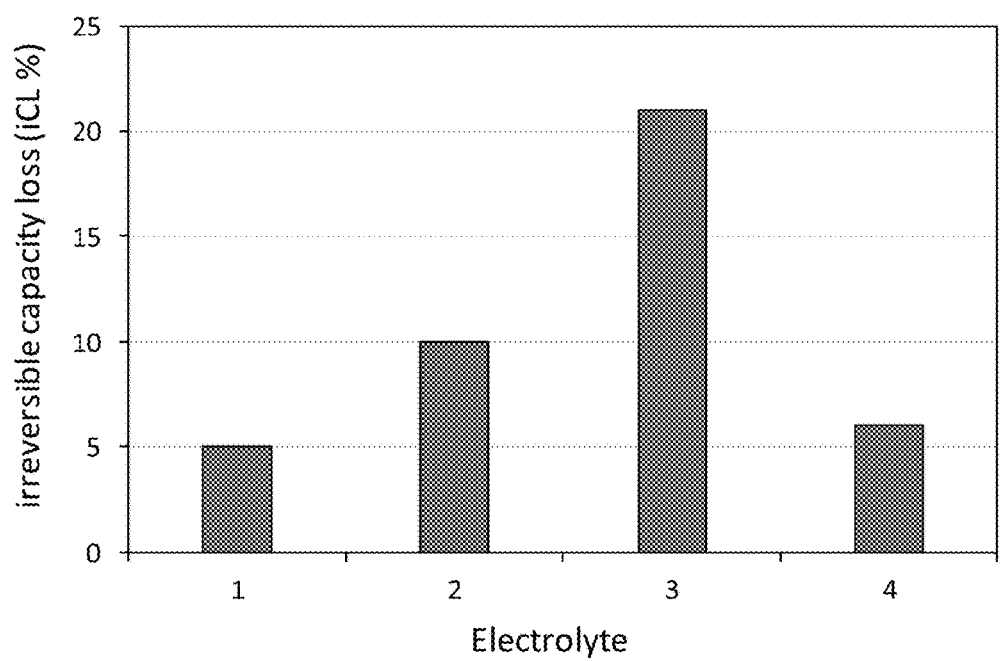
FIG. 1 is a bar graph of irreversible capacity loss % of a graphite anode vs the electrolyte compositions containing ionic liquids of Table 1.

The disclosure relates to the use of azepanium based ionic liquids and carbonate esters as a high performance, non-flammable, wide operating temperature range electrolyte formulation for electrochemical cells.

The present disclosure is directed towards an ionic liquid, and the cations have at least one azepanium functional moiety. The disclosure further includes a method for synthesizing the azepanium-functionalized cations, and the use of such functionalized cations in an ionic liquid for electrochemical cells. One key function of the present compounds that is distinct from other ionic liquids that are used in electrochemical cells is that the present compounds can operate over a larger temperature range than conventional compounds. The present compounds also provide improved electrochemical stability against the negative electrode in Li ion batteries. The present compounds can improve the electrochemical voltage stability and thermal stability of Li ion batteries and Lithium metal batteries.

Due to the strong interactions between the cations and the graphite surface and poor cathodic electrochemical stability, ionic liquids possessing longer alkyl tails and more imidazolium rings or aromatic ring are applied to form more stable and well-regulated layers at graphite surfaces.

One embodiment of the present disclosure appends an azepanium cation functional moiety to improve the electrochemical stability against the negative electrode of Li-ion batteries, and to create electrolyte formulations containing the functional azepanium-based ionic liquids as shown below:

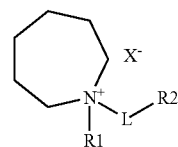

wherein $R_1$ is a $C_1$-$C_{16}$ alkyl, alkenyl, alkoxy, aryl, alkynyl, alkylsiloxy, alkylhalide, silyl, esters, carbonyl, phenyl or perfluoro group; L is a linker that is a $C_1$-$C_{16}$ alkyl, alkenyl, alkoxy, aryl, alkynyl, alkylsiloxy, alkylhailde, thioether, sulfoxide, azo, amino, silyl, esters, carbonyl, phenyl or perfluoro group; $R_2$ represents a functional moiety such as a halide, oxygen, nitrogen, sulfur, phosphorus, alkane, ester, partially or fully halogenated alkyl, ketone, carbonyl, alkoxyalkane, alkene, aryl, nitrile, silane, sulfone, thiol, phenol, hydroxyl, amine, imide, aldehyde, carboxylic acid, alkyne, carbonate or anhydride, wherein any of the carbon or hydrogen atoms in the moieties are further substituted with halides, oxygen, nitrogen, sulfur, phosphorus, alkanes, esters, ethers, ketones, carbonyls, alkoxyalkanes, alkenes, aryls, nitriles, silanes, sulfones, thiols, phenols, hydroxyls, amines, imides, aldehydes, carboxylic acids, alkynes, carbonates or anhydrides; and $X^-$ represents the anion of the ionic compound and includes halides, aluminates, arsenides, cyanides, thiocyanates, nitrites, benzoates, chlorates, chlorites, chromates, sulfates, sulfites, silicates, thiosulfates, oxalates, acetates, formates, hydroxides, nitrates, phosphates, imides, borates or phosphazines.

Suitable anions, $X^-$, of the ionic liquid compound include bis(trifluoromethylsulphonyl)imide, dicyanamide, hexahalophosphates (conveniently hexafluorophosphate or hexachlorophosphate), tetrahaloborates (tetrafluoroborate or tetrachloroborate), carbonates, sulfonates or carboxylates.

Electrolyte Composition: For the present disclosure, an electrolyte includes a thermally stable ionic liquid, an alkali metal salt, a polymer and aprotic solvents, which are all used in the electrochemical cell. The ionic liquid contains an organic cation and inorganic/organic anion, with the organic cation being N-alkyl-N-alkyl-pyrrolidinium, N-alkyl-N-alkyl-pyridinium, N-alkyl-N-alkyl-sulfonium, N-alkyl-N-alkyl-ammonium, N-alkyl-N-alkyl-piperidinium or the like, and the anion being tetrafluoroborate, hexafluorophosphate, bis(trifluoromethylsulfonyl)imide, bis(pentafluoroethylsulfonyl)imide, trifluoroacetate or the like. The polymer in the electrolyte includes poly(ethylene glycol) derivatives, with varying molecular weights ranging from 150 to 10,000,000 g/mol. Suitable aprotic solvents include carbonates, ethers, acetamides, acetonitrile, symmetric sulfones, 1,3-dioxolanes, dimethoxyethanes, glymes, siloxanes and their blends. The alkali metal salt can be $LiBF_4$, $LiNO_3$, $LiPF_6$, $LiAsF_6$, lithium bis(trifluoromethylsulfonyl)imide (LiTFSI), lithium bis(pentafluoroethylsulfonyl)imide, lithium trifluoroacetate or a similar compound. Alternatively, the aprotic organic solvent includes open-chain or cyclic carbonates, carboxylic acid esters, nitriles, ethers, sulfones, ketones, lactones, dioxolanes, glymes, crown ethers, siloxanes, phosphoric acid esters, phosphates, phosphites, mono- or polyphosphazenes or mixtures thereof.

In some embodiments, the electrolyte includes a lithium salt in addition to the ionic liquid. A variety of lithium salts may be used including, for example, $Li[CF_3CO_2]$; $Li[C_2F_5CO_2]$; $Li[ClO_4]$; $Li[BF_4]$; $Li[AsF_6]$; $Li[PF_6]$; $Li[PF_2(C_2O_4)_2]$; $Li[PF_4C_2O_4]$; $Li[CF_3SO_3]$; $Li[N(CP_3SO_2)_2]$; $Li[C(CF_3SO_2)_3]$; $Li[N(SO_2C_2F_5)_2]$; lithium alkyl fluorophosphates; $Li[B(C_2O_4)_2]$; $Li[BF_2C_2O_4]$; $LI_2[B_{12}Z_{12-j}H_j]$; $Li_2[B_{10}X_{10-j'}H_{j'}]$ or a mixture of any two or more thereof, wherein Z is independently at each occurrence a halogen, j is an integer from 0 to 12 and j' is an integer from 1 to 10. Alternatively, the alkali metal salt can be lithium, sodium, aluminum or magnesium.

In some applications of the present electrolyte, such as a formulation for a lithium ion battery, aprotic solvents are combined with the present ionic liquids to decrease the viscosity and increase the conductivity. Aprotic solvents lack exchangeable protons and include cyclic carbonic acid esters, linear carbonic acid esters, phosphoric acid esters, phosphates, phosphites, mono- or polyphosphazenes, oligoether-substituted siloxanes/silanes, cyclic ethers, chain ethers, lactone compounds, chain esters, nitrile compounds, amide compounds, sulfone compounds and the like. These solvents may be used singly, or at least two of them in admixture. Examples of aprotic solvents or carriers for forming the electrolyte systems include but are not limited to dimethyl carbonate, ethyl methyl carbonate, diethyl carbonate, methyl propyl carbonate, ethyl propyl carbonate, dipropyl carbonate, bis(trifluoroethyl) carbonate, bis(pentafluoropropyl) carbonate, trifluoroethyl methyl carbonate, pentafluoroethyl methyl carbonate, heptafluoropropyl methyl carbonate, perfluorobutyl methyl carbonate, trifluoroethyl ethyl carbonate, pentafluoroethyl ethyl carbonate, heptafluoropropyl ethyl carbonate, perfluorobutyl ethyl carbonate, etc., fluorinated oligomers, methyl propionate, ethyl propionate, butyl propionate, dimethoxyethane, triglyme, dimethylvinylene carbonate, tetraethyleneglycol, dimethyl ether, polyethylene glycols, triphenyl phosphate, tributyl phosphate, hexafluorocyclotriphosphazene, 2-Ethoxy-2,4,4,6,6-pentafluoro-1,3,5,2λ5,4λ5,6λ5triazatriphosphinine, triphenyl phosphite, sulfolane, dimethyl sulfoxide, ethyl methyl sulfone, ethylvinyl sulfone, allyl methyl sulfone, divinyl sulfone, fluorophynelmethyl sulfone and gamma-butyrolactone.

In some embodiments, the electrolytes further include an electrode stabilizing additive to protect the electrodes from degradation. Thus, electrolytes of the present technology may include an electrode stabilizing additive that is reduced or polymerized on the surface of a negative electrode to form a passivation film on the surface of the negative electrode. Likewise, electrolytes can include an electrode stabilizing additive that can be oxidized or polymerized on the surface of the positive electrode to form a passivation film on the surface of the positive electrode. In some embodiments, electrolytes of the present technology further include mixtures of the two types of electrode stabilizing additives.

In some embodiments, an electrode-stabilizing additive is a substituted or unsubstituted linear, branched or cyclic hydrocarbon including at least one oxygen atom and at least one aryl, alkenyl or alkynyl group. The passivating film formed from such electrode stabilizing additives may also be formed from a substituted aryl compound or a substituted or unsubstituted heteroaryl compound, where the additive includes at least one oxygen atom. A combination of two additives may also be used. In some such embodiments, one additive is selective for forming a passivating film on the cathode to prevent leaching of metal ions and the other additive can be selective for passivating the anode surface to prevent or lessen the reduction of metal ions at the anode. Alternatively, the additive could be sulfur-containing compounds, phosphorous-containing compounds, boron-containing compounds, silicon-containing compounds, nitrogen-containing heterocyclic compounds, compounds containing an unsaturated carbon-carbon bond, carboxylic acid anhydrides or mixtures thereof.

Representative electrode stabilizing additives include glyoxal bis(diallyl acetal), Tetra(ethylene glycol) divinyl ether, 1,3,5-Triallyl-1,3,5-triazine-2,4,6(1H,3H,5H)-trione, 1,3,5,7-Tetravinyl-1,3,5,7-tetramethylcyclotetrasiloxane, 2,4,6-Triallyloxy-1,3,5-Triazine, 1,3,5-Triacryloylhexahydro-1,3,5-triazine, 1,2-divinyl furoate, 1,3-butadiene carbonate, 1-vinylazetidin-2-one, 1-vinylaziridin-2-one, 1-vinylpiperidin-2-one, 1 vinylpyrrolidin-2-one, 2,4-divinyl-1,3-dioxane, 2 amino-3 vinylcyclohexanone, 2-amino-3-vinylcyclopropanone, 2 amino-4-vinylcyclobutanone, 2-amino-5-vinylcyclopentanone, 2-aryloxy-cyclopropanone, 2-vinyl-[1,2]oxazetidine, 2 vinylaminocyclohexanol, 2-vinylaminocyclopropanone, 2 vinyloxetane, 2-vinyloxy-cyclopropanone, 3-(N-vinylamino)cyclohexanone, 3,5-divinyl furoate, 3-vinylazetidin-2-one, 3 vinylaziridin 2 one, 3 vinylcyclobutanone, 3 vinylcyclopentanone, 3 vinyloxaziridine, 3 vinyloxetane, 3-vinylpyrrolidin-2-one, 2-Vinyl-1,3-dioxolane, Acrolein diethyl acetal, Acrolein dimethyl acetal, 4,4 divinyl-3 dioxolan 2-one, 4 vinyltetrahydropyran, 5-vinylpiperidin-3-one, allylglycidyl ether, butadiene monoxide, butyl vinyl ether, dihydropyran-3-one, divinyl butyl carbonate, divinyl carbonate, divinyl crotonate, divinyl ether, divinyl ethylene carbonate, divinyl ethylene silicate, divinyl ethylene sulfate, divinyl ethylene sulfite, divinyl methoxypyrazine, divinyl methylphosphate, divinyl propylene carbonate, ethyl phosphate, methoxy-o-terphenyl, methyl phosphate, oxetan-2-yl-vinylamine, oxiranylvinylamine, vinyl carbonate, vinyl crotonate, vinyl cyclopentanone, vinyl ethyl-2-furoate, vinyl ethylene carbonate, vinyl ethylene silicate, vinyl ethylene sulfate, vinyl ethylene sulfite, vinyl methacrylate, vinyl phosphate, vinyl-2-furoate, vinylcyclopropanone, vinylethylene oxide, beta-vinyl-gamma-butyrolactone, succinic anhydride, maleic anhydride, 1,3-propane sultone, 1,3-propene sultone, 1,3,2-dioxathiolane-2,2-dioxide, 4-fluoro-1,3-dioxolan-2-one, tris(trimethylsilyl) phosphite, triphenyl phosphite, triphenyl phosphate, 3,3,3-trifluoropropyl)trimethoxysilane, trimethylsilyl trifluoromethanesulfonate, tris(trimethylsilyl) borate, tripropyl phosphate, or a mixture of any two or more thereof. In some embodiments, the electrode-stabilizing additive may be a cyclotriphosphazene that is substituted with F, alkyloxy, alkenyloxy, aryloxy, methoxy, allyloxy groups or combinations thereof. For example, the additive may be a (divinyl)(methoxy)(trifluoro) cyclotriphosphazene, (trivinyl)(difluoro)(methoxy)cyclotriphosphazene, (vinyl)(methoxy)(tetrafluoro)cyclotriphosphazene, (aryloxy)(tetrafluoro)(methoxy)cyclotriphosphazene, (diaryloxy)(trifluoro)(methoxy)cyclotriphosphazene compounds, or a mixture of two or more such compounds. In some embodiments, the electrode stabilizing additive is vinyl ethylene carbonate, vinyl carbonate, or 1,2-diphenyl ether, or a mixture of any two or more such compounds.

Other representative electrode stabilizing additives may include compounds with phenyl, naphthyl, anthracenyl, pyrrolyl, oxazolyl, furanyl, indolyl, carbazolyl, imidazolyl or thiophenyl, fluorinated carbonates, sultone, sulfide, anhydride, silane, siloxy, phosphate, and phosphite groups. For example, electrode stabilizing additives may be Phenyl Trifluoromethyl Sulfide, Fluoroethylene carbonate, 1,3,2-Dioxathiolane 2,2-Dioxide, 1-Propene 1,3-Sultone, 1,3-Propanesultone, 1,3-Dioxolan-2-one, 4-[(2,2,2-trifluoroethoxy)methyl], 1,3-Dioxolan-2-one, 4-[[2,2,2-trifluoro-1-(trifluoromethyl)ethoxy]methyl]-, Methyl 2,2,2-trifluoroethyl carbonate, Nonafluorohexyltriethoxysilane, Octamethyltrisiloxane, Methyltris(trimethylsiloxy)silane, Tetrakis(trimethylsiloxy)silane, (Tridecafluoro-1,1,2,2-tetrahydrooctyl)triethoxysilane, Tris(1H. 1H-heptafluorobutyl) phosphate, 3,3,3-Trifluoropropyltris(3,3,3-Trifluoropropyldimethylsiloxy)Silane, (3,3,3-Trifluoropropyl)Trimethoxysilane, Trimethylsilyl Trifluoromethanesulfonate, Tris(trimethylsilyl) Borate, Tripropyl Phosphate, Bis(Trimethylsilylmethyl)Benzylamine, Phenyltris(Trimethylsiloxy)Silane, 1,3-Bis(Trifluoropropyl)Tetramethyldisiloxane, Triphenyl phosphate, Tris(Trimethylsilyl)Phosphate, Tris(1H. 1H,5H-octafluoropentyl) phosphate, Triphenyl Phosphite, Trilauryl Trithiophosphite, Tris(2,4-di-tert-butylphenyl) Phosphite, Tri-p-tolyl Phosphite, Tris(2,2,3,3,3-pentafluoropropyl)phosphate, Succinic Anhydride, 1,5,2,4-Dioxadithiane 2,2,4,4-tetraoxide, Tripropyl Trithiophosphate, aryloxpyrrole, aryloxy ethylene sulfate, aryloxy pyrazine, aryloxy-carbazole trivinylphosphate, aryloxy-ethyl-2-furoate, aryloxy-o-terphenyl, aryloxy-pyridazine, butyl-aryloxy-ether, divinyl diphenyl ether, (tetrahydrofuran-2-yl)-vinylamine, divinyl methoxybipyridine, methoxy-4-vinylbiphenyl, vinyl methoxy carbazole, vinyl methoxy piperidine, vinyl methoxypyrazine, vinyl methyl carbonate-allylanisole, vinyl pyridazine, 1-divinylimidazole, 3-vinyltetrahydrofuran, divinyl furan, divinyl methoxy furan, divinylpyrazine, vinyl methoxy imidazole, vinylmethoxy pyrrole, vinyl-tetrahydrofuran, 2,4-divinyl isooxazole, 3,4 divinyl-1-methyl pyrrole, aryloxyoxetane, aryloxy-phenyl carbonate, aryloxy-piperidine, aryloxy-tetrahydrofuran, 2-aryl-cyclopropanone, 2-diaryloxy-furoate, 4-allylanisole, aryloxy-carbazole, aryloxy-2-furoate, aryloxy-crotonate, aryloxy-cyclobutane, aryloxy-cyclopentanone, aryloxy-cyclopropanone, aryloxy-cycolophosphazene, aryloxy-ethylene silicate, aryloxy-ethylene sulfate, aryloxy-ethylene sulfite, aryloxy-imidazole, aryloxy-methacrylate, aryloxy-phosphate, aryloxy-pyrrole, aryloxyquinoline, diaryloxycyclotriphosphazene, diaryloxy ethylene carbonate, diaryloxy furan, diaryloxy methyl phosphate, diaryloxy-butyl carbonate, diaryloxy-crotonate, diaryloxy-diphenyl ether, diaryloxy-ethyl silicate, diaryloxy-ethylene silicate, diaryloxy-ethylene sulfate, diaryloxyethylene sulfite, diaryloxy-phenyl carbonate, diaryloxy-propylene carbonate, diphenyl carbonate, diphenyl diaryloxy silicate, diphenyl divinyl silicate, diphenyl ether, diphenyl silicate, divinyl methoxydiphenyl ether, divinyl phenyl carbonate, methoxycarbazole, or 2,4-dimethyl-6-hydroxy-pyrimidine, vinyl methoxyquinoline, pyridazine, vinyl pyridazine, quinoline, vinyl quinoline, pyridine, vinyl pyridine, indole, vinyl indole, triethanolamine, 1,3-dimethyl butadiene, butadiene, vinyl ethylene carbonate, vinylene carbonate, imidazole, vinyl imidazole, piperidine, vinyl piperidine, pyrimidine, vinyl pyrimidine, pyrazine, vinyl pyrazine, isoquinoline, vinyl isoquinoline, quinoxaline, vinyl quinoxaline, biphenyl, 1,2-diphenyl ether, 1,2-diphenylethane, o-terphenyl, N-methyl pyrrole, naphthalene or a mixture of any two or more such compounds.

In other embodiments, the electrolyte of the present technology includes an aprotic gel polymer carrier/solvent. Suitable gel polymer carrier/solvents include polyethers, polyethylene oxides, polyimides, polyphosphazines, polyacrylonitriles, polysiloxanes, polyether grafted polysiloxanes, derivatives of the foregoing, copolymers of the foregoing, cross-linked and network structures of the foregoing, blends of the foregoing and the like, to which is added a suitable ionic electrolyte salt. Other gel-polymer carrier/solvents include those prepared from polymer matrices derived from polypropylene oxides, polysiloxanes, sulfonated polyimides, perfluorinated membranes (Nafion resins), divinyl polyethylene glycols, polyethylene glycol-bis-(methyl acrylates), polyethylene glycol-bis(methyl methacrylates), derivatives of the foregoing, copolymers of the foregoing and cross-linked and network structures of the foregoing.

The present functional ionic liquids and the electrolytic solution containing the salt are high in electrical conductivity and solubility in organic solvents, and are suitable for use as an electrolytic solution for electrochemical devices. Examples of electrochemical devices are electric double-layer capacitor, secondary batteries, solar cells of the pigment sensitizer type, electrochromic devices, condensers, etc., and this list is nevertheless not limitative. These ILs are especially suitable as electrochemical devices that are electric double-layer capacitor and secondary batteries such as lithium ion batteries.

The disclosure will be further illustrated with reference to the following specific examples. It is understood that these examples are given by way of illustration and are not meant to limit the disclosure or the claims to follow.

EXAMPLE 1

In this example, the synthesis of $AZ_{13}COO1$-TFSI, an example of a compound in accordance with the present disclosure is shown. The first step describes the synthesis of N-methylbutyrate azepane, and then the second step describes the synthesis of $AZ_{13}COO1$-TFSI using N-methylbutyrate azepane as a precursor. The synthesis of two comparative compounds $Pyr_{13}COO1$ (Comparative Example A) and $PP_{13}COO1$ (Comparative Example B), are then described.

Synthesis of $AZ_{13}COO1$-TFSI

Step 1: Synthesis of N-methylbutyrate Azepane

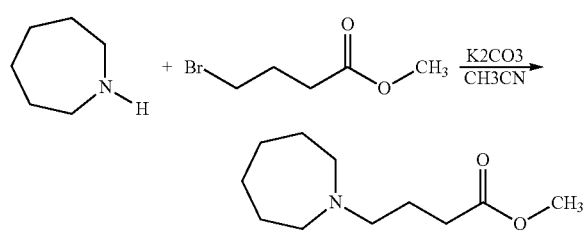

| Reagent | MW | Equiv | Mol | Mass (g) | Density | Volume (mL) | Conc | Yield (Calc) |
|---|---|---|---|---|---|---|---|---|
| azepane | 98.18 | 1.00 | 0.040 | 4.0 | 0.825 | 4.8 | | |
| methyl-4-bromobutyrate | 181.03 | 1.00 | 0.040 | 7.3 | 1.434 | 5.1 | | |
| $K_2CO_3$ | 138.21 | 1.05 | 0.042 | 5.9 | | | 0% | |
| N-methylbutyrate azepane | 199.3 | 1.00 | 0.000 | | | | | 8.0 |
| KBr | 119.00 | 1.00 | | | | | | 4.80 |
| $KHCO_3$ | 100.11 | 1.00 | | | | | | 4.04 |

To a 250 mL flask equipped with a magnetic stirring bar, azepane, anhydrous acetonitrile (20 mL), methyl-4-bromobutyrate and potassium carbonate were added. A slight temperature increase was observed. The mixture was stirred at room temperature and the overall reaction time was 4 days.

As the reaction proceeded, potassium carbonate was gradually consumed as it scavenged the liberated HBr to form potassium bromide (4.8 g) and potassium bicarbonate (4.0 g).

DCM (10 mL) was added and the solid was collected by vacuum filtration. The organic phase was washed with deionized water (10 mL), separated, dried over $MgSO_4$ and filtered, and the solvent was stripped using rotary evaporation. Yield: pale oil, 7.9 g, (>99%).

Characterization. FTIR: C=O, 1737, C—O, 1177 $cm^{-1}$.
$H^+$ NMR: ($CDCl_3$) δ ppm 3.67 (s, 3H), 2.61 (t, 4H), 2.48 (t, 2H), 2.34 (t, 2H), 1.77 (q, 2H), 1.62-1.58 (m, 8H).

Step 2: Synthesis of $AZ_{13}COO1$-TFSI

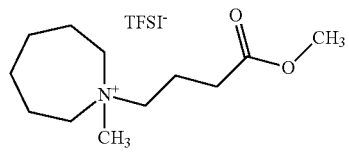

| Reagent | MW | Equiv | Mol | Mass (g) | Density | Volume (mL) | Conc | Yield (Calc) |
|---|---|---|---|---|---|---|---|---|
| N-methylbutyrate azepane | 199.30 | 1.00 | 0.040 | 8.0 | | 8.0 | | |
| methyliodide | 141.94 | 1.00 | 0.040 | 5.7 | 2.28 | 2.5 | | |
| acetonitrile | | | | 27.4 | 0.786 | 34.9 | 50% | |
| $AZ_{13}COO1$-I | 341.24 | 1.00 | 0.035 | 12.0 | | | | 13.7 |
| DI water | | | | 28.3 | 1.00 | 28.3 | 80% | |
| LiTFSI | 287.09 | 1.05 | 0.037 | 10.6 | | | | |
| $AZ_{13}COO1$-TFSI | 494.48 | | | | | | | 17.4 |

Quaternization. To a 250 mL 3-neck flask equipped with a magnetic stirring bar, water-cooled condenser, $N_2$ inlet and a thermocouple, N-methylbutyrate azepane (NB2-76-1) and acetonitrile were added.

While stirring at room temperature, methyliodide was added to the mixture and the internal temperature was monitored for evidence of exotherm. The temperature was maintained at 32° C.

The mixture formed a clear light yellow solution. The overall reaction time was about 2 hours.

The mixture was cooled to room temperature and the solvent was stripped using rotary evaporation to a yellow oil. The mixture was pumped under high vacuum to further remove the solvent and was cooled for 16 hours at 40° C.; this produced a yellow solid. The solid was dispersed in dry acetone (60 mL) and became white crystals. The solid was collected by vacuum filtration and rinsed with dry acetone (10 mL). The mother liquor removed all of the yellow color. Yield: white solid, 12.0 g (88%). Combined yield from previous reaction: 14.5 g. H⁺ NMR: (CDCl3) δ ppm 3.79 (t, 2H), 3.70 (m, 7H), 3.37 (s, 3H), 2.60 (t, 2H), 2.14 (m, 2H), 2.02 (m, 4H), 1.80 (m, 4H).

Metathesis. To a 100 mL-capped bottle equipped with a magnetic stirring bar, the iodide from step 1 and lithium bis(trifluoromethylsulfonyl)imide were added as two separate solutions, each dissolved in 30 mL deionized water. When the two solutions were combined, a cloudy precipitate quickly formed and a dense pale layer deposited on the bottom. The mixture was stirred at room temperature for 16 hours.

The water layer was decanted, DCM (20 mL) was added and the entire mixture was poured into a separatory funnel. The organic layer was washed with DI water (2×20 mL), separated and dried over MgSO₄. The solvent was stripped by rotary evaporation and pumped under high vacuum by a vacuum oven (5 mbar, 60° C.). Yield: pale white oil, 16.6 g (95%).

Characterization. FTIR: C=O, 1733, C—O, 1177 cm-1, Silver halide test: negative, Karl Fischer: 85 ppm H⁺ NMR: (CDCl3) δ ppm 3.70 (s, 3H), 3.50 (t, 2H), 3.48-3.36 (m, 4H), 3.06 (s, 3H), 2.48 (t, 2H), 2.06 (m, 2H), 1.92 (m, 4H), 1.74 (m, 4H). F-NMR: (CDCl3) δ ppm -78.91 (s).

COMPARATIVE EXAMPLE A

Synthesis of Pyr₁₃COO1 TFSI

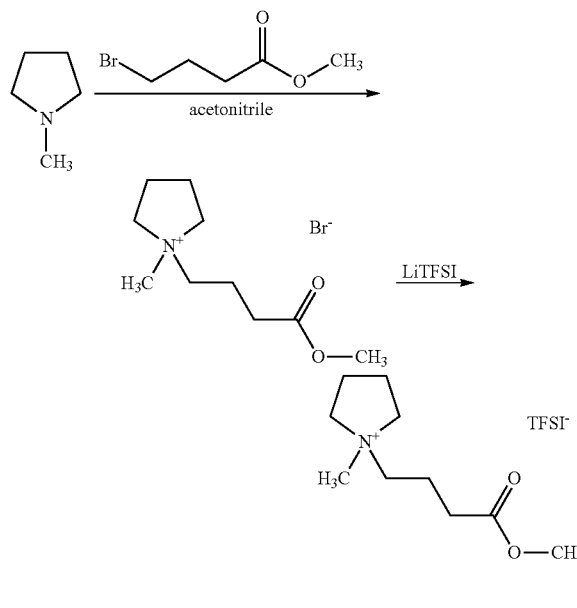

Quaternization. To a 500 mL 3-neck flask equipped with a magnetic stirring bar, water-cooled condenser, N₂ inlet and thermocouple, 1-methyl pyrrolidine and acetonitrile were added.

While stirring at room temperature, methyl-4-bromobutyrate was added to the mixture and the internal temperature was monitored for evidence of exotherm. No temperature

| Reagent | MW | Equiv | Mol | Mass (g) | Density | Volume (mL) | Conc | Yield (Calc) |
|---|---|---|---|---|---|---|---|---|
| 1-methylpyrrolidine | 85.15 | 1.00 | 0.329 | 28.0 | 0.80 | 35.0 | | |
| methyl-4-bromobutyrate | 181.03 | 1.00 | 0.329 | 59.5 | 1.43 | 41.5 | | |
| acetonitrile | | | | 109.4 | 0.79 | 139.2 | 50% | |
| Pyr₁₃COO1-Br | 266.18 | 1.00 | 0.289 | 77.0 | | | | 87.5 |
| DI water | | | | 182.4 | 1.00 | 182.4 | 90% | |
| LiTFSI | 287.09 | 1.05 | 0.304 | 87.2 | | | | |
| Pyr₁₃COO1-TFSI | 466.43 | | | | | | | 134.9 | increase was observed.

The mixture was heated in an oil bath so that the internal temperature was approx. 60° C. The mixture formed a clear yellow solution. The overall reaction time was about 7 hours.

The mixture was cooled to room temperature and the solvent was stripped by rotary evaporation to a yellow oil. Stirring seed crystals with a glass rod and cooling at 40° C. produced a yellow solid. The solid was dispersed in dry acetone (60 mL) and became white crystals. The solid was collected by vacuum filtration and the mother liquor removed all of the yellow color. Yield: white solid, 77.0 g (88%).

Metathesis. To a 500 mL round bottom flask equipped with a magnetic stirring bar, the bromide from step 1 and lithium bis(trifluoromethylsulfonyl)imide [Is this TFSI?] were added as two separate solutions, each dissolved in 100 mL deionized water. The two solutions were combined and a cloudy precipitate quickly formed, after which a dense pale layer deposited on the bottom. The mixture was stirred at room temperature for 4 hours.

The water layer was decanted, DCM (100 mL) was added and the entire mixture was poured into a separatory funnel. The organic layer was washed with deionized water (2×40 mL), separated, dried over MgSO₄ and stirred in activated decolorizing carbon for 18 hours. The mixture was filtered on a bed of MgSO₄ and the solvent was stripped by rotary evaporation. Yield: clear, colorless oil, 124.8 g (93%).

Characterization. FTIR: C=O, 1733, C—O 1177 cm-1, Silver halide test: negative, Viscosity: 143.9 cP @ 25° C. (5.0 rpm), 71.8 cP @ 40° C. (5.0 rpm), 23.5 cP @ 70° C. (5.0 rpm), Density=1.4346 g/mL.

H⁺ NMR: (CDCl3) (trans isomer) δ ppm 3.70 (s, 3H), 3.55 (m, 4H), 3.41 (m, 2H), 3.09 (s, 3H), 2.48 (t, 2H), 2.28 (m, 4H), 2.07 (m, 2H). (cis isomer) δ ppm 3.66 (s, 3H), 3.51 (m, 4H), 3.35 (m, 2H), 3.04 (s, 3H), 2.43 (t, 2H), 2.24 (m, 4H), 2.07 (m, 2H).

COMPARATIVE EXAMPLE B

Synthesis of PP$_{13}$COO1 TFSI

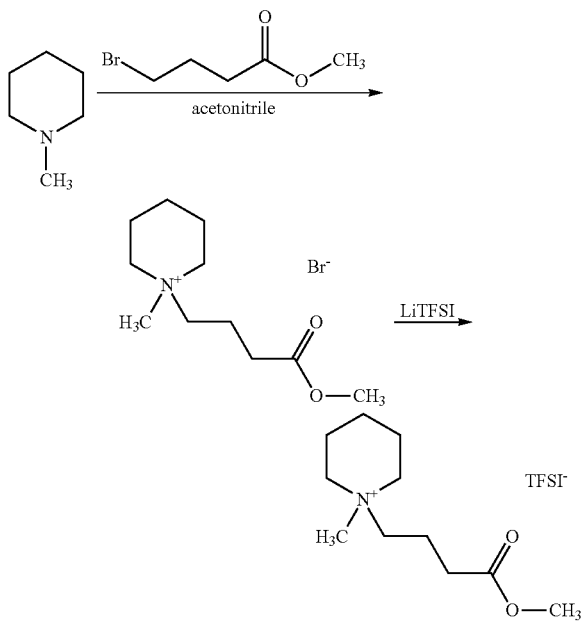

| Reagent | MW | Equiv | Mol | Mass (g) | Density | Volume (mL) | Conc | Yield (Calc) |
|---|---|---|---|---|---|---|---|---|
| N-methylpiperidine | 99.17 | 1.00 | 0.202 | 20.0 | 0.816 | 24.5 | | |
| methyl-4-bromobutryate | 181.03 | 1.00 | 0.202 | 36.5 | 1.434 | 25.5 | | |
| acetonitrile | | | | 70.6 | 0.786 | 89.9 | 80% | |
| PP$_{13}$COO1-Br | 280.20 | 1.00 | 0.185 | 51.8 | | | | 56.5 |
| DI water | | | | 119.5 | 1.00 | 119.5 | 90% | |
| LiTFSI | 278.09 | 1.05 | 0.194 | 55.7 | | | | |
| PP$_{13}$COO1-TFSI | 480.45 | | | | | | | 88.8 |

Quaternization. To a 500 mL 3-neck flask equipped with a magnetic stirring bar, water-cooled condenser, N$_2$ inlet and thermocouple, N-methyl piperidine and acetonitrile were added. While stirring at room temperature, methyl-4-bromobutyrate was added to the mixture and the internal temperature was monitored for evidence of exotherm. No temperature increase was observed.

The mixture was heated using an oil bath until the internal temperature was approximately 60° C. The mixture formed a clear yellow solution. The overall reaction time was about 7 hours.

The mixture was cooled to room temperature and the solvent was stripped by rotary evaporation to a yellow oil. The mixture was pumped under high vacuum to further remove solvent. Cooling 16 hours at 40° C. produced a yellow solid. The solid was dispersed in dry acetone (60 mL) and became white crystals. The solid was collected by vacuum filtration and rinsed with dry acetone (10 mL). The mother liquor removed all of the yellow color. Yield: white solid, 51.8 g (92%).

Metathesis. To a 250 mL capped bottle equipped with a magnetic stirring bar, the bromide from step 1 and lithium bis(trifluoromethylsulfonyl)imide were added as two separate solutions, and each was dissolved in 50 mL deionized water. When the two solutions were combined, a cloudy precipitate quickly formed and a dense pale yellow layer deposited on the bottom. The mixture was stirred at room temperature for 3 hours.

The oil crystallized into a white solid. DCM (80 mL) was added and the entire mixture was poured into a separatory funnel. The organic layer was washed with deionized water (2×40 mL), separated, dried over MgSO$_4$ and treated with activated decolorizing carbon. The mixture was then stirred at room temperature for 5 days. The mixture was filtered on a bed of MgSO$_4$ and the solvent was stripped by rotary evaporation. The oil was crystallized at room temperature to a white solid. The solid was pumped under high vacuum for 2 hours and by vacuum oven for 16 hours (5 mbar, 60° C.). Yield: pale oil (crystallizes to white solid at RT), 82.0 g (92%).

Characterization. FTIR: C=O, 1733, C—O, 1177 cm-1, Silver halide test: negative, Karl Fischer: 25.4 ppm.

H$^+$ NMR: (CDCl3) δ ppm 3.70 (s, 3H), 3.39 (m, 6H), 3.07 (s, 3H), 2.48 (t, 2H), 2.03 (m, 2H), 1.91 (m, 4H), 1.73 (m, 2H). F$^{19}$ NMR: (CDCl3) δ ppm −79.0 (s).

EXAMPLE 2

Electrochemical Stability. From the foregoing Example 1, the synthesized azepanium cation-based ionic liquids (AZ$_{13}$COO1-TFSI) were compared to pyrrolidinium (Pyr$_{13}$COO1-TFSI; Comparative Example A) and piperidinium (PP$_{13}$COO1-TFSI; Comparative Example B) cation-based ionic liquids as shown in the following procedure.

Electrolyte formulations were prepared in a dry argon filled glovebox by combining all the electrolyte components in a vial and stirring for 24 hours to ensure complete dissolution of the salts. The ionic liquid is added to a base electrolyte formulation comprising a 3:7 by weight mixture of ethylene carbonate, "EC", and ethyl methyl carbonate, "EMC", with 1 M lithium hexafluorophosphate, "LiPF$_6$", dissolved therein. The electrolyte formulations prepared are summarized in Table 1.

TABLE 1

Electrolyte comparisons

| Electrolyte | Base | Ionic liquid Additive (16 wt. %) | | |
|---|---|---|---|---|
| 1 | 1 M Li PF$_6$; EC:EMC; 3:7 w/w | NONE | | |
| 2 | 1 M Li PF$_6$; EC:EMC; 3:7 w/w | 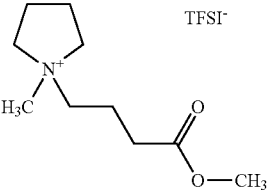 | TFSI$^-$ | Comparative Example A |
| 3 | 1 M Li PF$_6$; EC:EMC; 3:7 w/w | 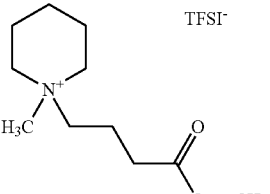 | TFSI$^-$ | Comparative Example B |
| 4 | 1 M Li PF$_6$; EC:EMC; 3:7 w/w | 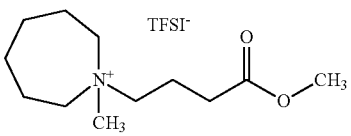 | TFSI$^-$ | Example 1 |

The electrolyte formulations prepared are used as the electrolyte in CR2032 coin cells including Lithium metal anode and graphite as the active material. In each cell 60 micro liters of electrolyte formulation is added and allowed to soak in the cell for 1 hour prior to sealing. The cells were then charged to 1.5 V and discharged to 0.005 V at a C/20 rate for the first cycles, and C/2 onwards. Initial cycle capacity loss or irreversible capacity loss (iCL) represented by the ratio between discharge capacity and charge capacity to the discharge capacity times 100. iCL signifies the stability of electrolyte towards graphite anode. A higher iCL suggests higher reactivity of electrolyte against graphite electrode. FIG. 1 compares average iCL values for electrolyte compositions shown in Table 1. Azepanium cation containing ionic liquid showed negligible change in iCL compared to base line electrolyte without any ionic liquid additives. This suggests the electrochemical stability of azepanium ionic liquids against negative electrodes. Therefore, the azepanium cations (AZ$_{13}$COO1-TFSI) of Example 1 improve electrochemical stability in lithium-ion batteries over previously known cations.

Figure 2:
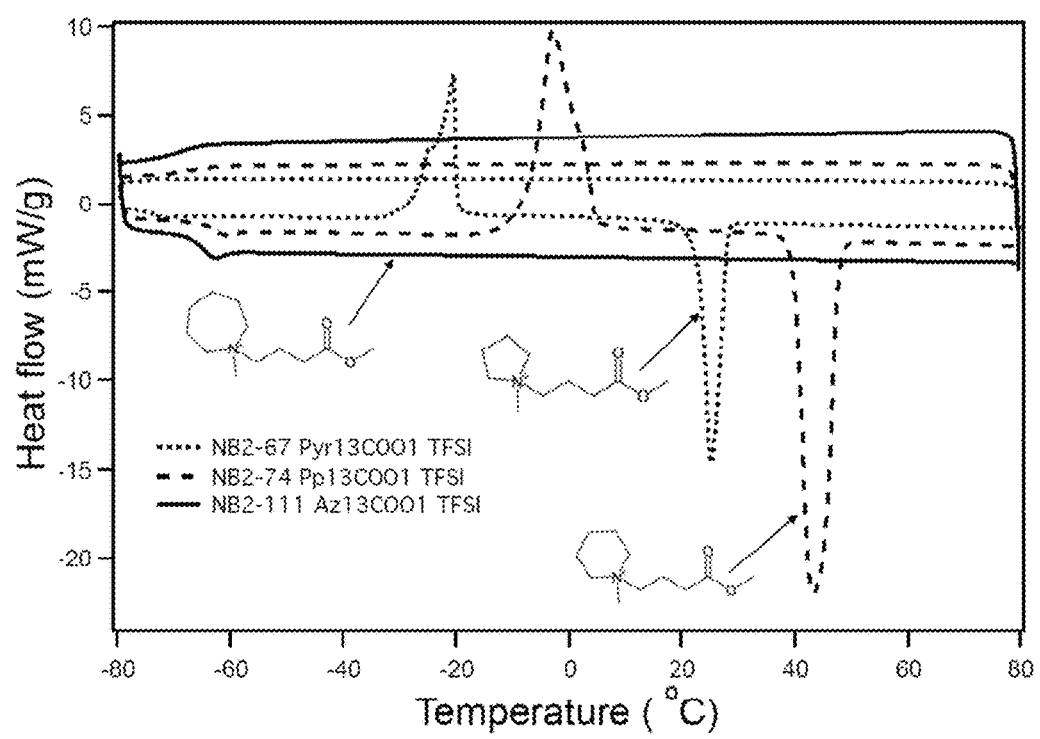
FIG. 2 illustrates differential scanning calorimetry test results for cyclic ammonium cations functionalized with an ester group.

Differential scanning calorimetry (DSC) was employed to measure the phase transitions of the functional ionic liquids with varying ring size (pyrrolidinium, piperidinium and azepanium). FIG. 2 depicts the DSC test results for different ring size cyclic ammonium cations functionalized with ester group. As shown by FIG. 2, azepanium cation-based ionic liquids (AZ$_{13}$COO1-TFSI; Comparative Example A) do not show crystallization or melting (represented by the peaks and valleys depicted) compared to pyrrolidinium (Pyr$_{13}$COO1-TFSI; Comparative Example A) and piperidinium (PP$_{13}$COO1-TFSI; Comparative Example B) cation-based ionic liquids. Therefore, the azepanium cations (AZ$_{13}$COO1-TFSI) of Example 1 improve thermal stability of electrolytes by expanding the operating temperature range of lithium-ion batteries over previously known cations.

Although various embodiments have been depicted and described in detail herein, it will be apparent to those skilled in the relevant art that various modifications, additions, substitutions and the like can be made without departing from the spirit of the disclosure and these are therefore considered to be within the scope of the disclosure as defined in the claims which follow.

What is claimed:

1. An ionic liquid compound comprising a cation and an anion according to formula:

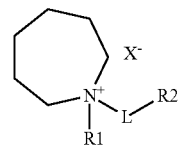

wherein R$_1$ is selected from the group comprising C$_1$-C$_{16}$ alkylsiloxy, silyl, ester, or perfluoro group;

wherein L is a linker comprising C$_1$-C$_{16}$ alkyl, alkenyl, alkoxy, aryl, alkynyl, alkylsiloxy, alkylhalide, thioether, sulfoxide, azo, amino, silyl, ester, carbonyl, phenyl or perfluoro group;

wherein R$_2$ represents a functional moiety comprising oxygen, nitrogen, sulfur, phosphorus, silane, sulfone, thiol, imide, carboxylic acid, carbonate or anhydride, wherein any of the carbon or hydrogen atoms in the moieties are further substituted with halide, oxygen, nitrogen, sulfur, ester, ketone, carbonyl, alkene, aryl, nitrile, silane, sulfone, thiol, phenol, hydroxyl, amine, imide, aldehyde, carboxylic acid, alkyne, carbonate or anhydride; and wherein $X^-$ represents an anion of the ionic compound comprising a halide, aluminate, arsenide, cyanide, thiocyanate, nitrite, benzoate, chlorate, chlorite, chromate, sulfate, sulfite, silicate, thiosulfate, oxalate, acetate, formate, hydroxide, nitrate, phosphate, imide, borate or phosphazines.

2. An electrolyte in an electrical energy storage device, the electrolyte comprising:
a) an aprotic organic solvent;
b) an alkali metal salt;
c) an additive; and
d) an ionic compound comprising a cation and an anion according to formula:

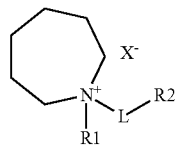

wherein $R_1$ is selected from the group comprising $C_1$-$C_{16}$ alkylsiloxy, alkylhalide, silyl, ester or perfluoro group;

wherein L is a linker comprising $C_1$-$C_{16}$ alkyl, alkenyl, alkoxy, aryl, alkynyl, alkylsiloxy, alkylhalide, thioether, sulfoxide, azo, amino, silyl, ester, carbonyl, phenyl or perfluoro group;

wherein $R_2$ represents a functional moiety comprising halide, oxygen, nitrogen, sulfur, phosphorus, alkane, ester, silane, sulfone, thiol, imide, carboxylic acid, carbonate or anhydride, wherein any of the carbon or hydrogen atoms in the moieties are further substituted with halide, oxygen, nitrogen, sulfur, phosphorus, alkane, ester, ether, ketone, carbonyl, alkoxyalkane, alkene, aryl, nitrile, silane, sulfone, thiol, phenol, hydroxyl, amine, imide, aldehyde, carboxylic acid, alkyne, carbonate or anhydride; and wherein $X^-$ represents an anion of the ionic compound comprising a halide, aluminate, arsenide, cyanide, thiocyanate, nitrite, benzoate, chlorate, chlorite, chromate sulfate, sulfite, silicate, thiosulfate, oxalate, acetate, formate, hydroxide, nitrate, phosphate, imide, or borate phosphazines.

3. The electrolyte of claim 2, wherein the aprotic organic solvent comprises an open-chain or cyclic carbonate, carboxylic acid ester, nitrite, ether, sulfone, sulfoxide, ketone, lactone, dioxolane, glyme, crown ether, siloxane, phosphoric acid ester, phosphates, phosphites mono- or polyphosphazene or mixtures thereof.

4. The electrolyte of claim 2, wherein the cation of the alkali metal salt comprises lithium, sodium, aluminum or magnesium.

5. The electrolyte of claim 2, wherein the additive comprises a sulfur-containing compound, phosphorous-containing compound, boron-containing compound, silicon-containing compound, nitrogen-containing heterocyclic compound, compound containing unsaturated carbon-carbon bond, carboxylic acid anhydride or mixtures thereof.

* * * * *